United States Patent

Kiuchi et al.

[11] Patent Number: 6,065,343
[45] Date of Patent: May 23, 2000

[54] ULTRASONIC DETECTING METHOD FOR BEARING RING

[75] Inventors: Akihiro Kiuchi; Kikuaki Kamamura; Manabu Ohori, all of Kanagawa, Japan

[73] Assignee: NSK Ltd., Tokyo, Japan

[21] Appl. No.: 09/320,448

[22] Filed: May 27, 1999

[30] Foreign Application Priority Data

May 27, 1998 [JP] Japan .................................. 10-146180

[51] Int. Cl.[7] .................................................. G01N 29/00
[52] U.S. Cl. ................................................ 73/622; 73/620
[58] Field of Search ............................. 73/622, 620, 618,
73/596, 593, 570, 629, 627

[56] References Cited

U.S. PATENT DOCUMENTS 5,005,417  4/1991  Kawasaki et al. ........................ 73/593
5,056,368  10/1991  Kawasaki et al. ........................ 73/642

Primary Examiner—Richard A. Moller
Attorney, Agent, or Firm—Sughrue, Mion, Zinn, Macpeak & Seas, PLLC

[57] ABSTRACT

In an ultrasonic detecting method for a bearing ring in which a bearing ring 2 and an ultrasonic detection probe 3 are disposed within ultrasonic transmission medium such as water, then ultrasonic wave is transmitted from the ultrasonic detection probe 3 to the bearing ring 2, and a defect of the bearing ring 2 is detected on the basis of an ultrasonic wave echo reflected from the bearing ring 2, wherein at least a defect in a range from the surface of the bearing ring 2 to a position beneath by 2 mm from the surface of the bearing ring which is deeper than a maximum shearing stress position of the bearing ring 2 is detected by an angle beam method with an incident angle in a range of 10 to 30°, preferably in a range of 25 to 30°, and a defect in a range deeper than the range detected by the angle beam method is detected by a normal beam method with an incident angle in a range of 0 to 10°, preferably in a range of 0 to 5°, thereby to detect a defect in the entire section of the bearing ring 2.

7 Claims, 9 Drawing Sheets

DETECTING DIRECTION
DETECT
TP1
30

ULTRASONIC DETECTION RESULT NEAR SURFACE PERPENDICULAR DETECT (WATER DISTANCE 20mm)

DETECTING DIRECTION

DETECT

TP2

40

ULTRASONIC DETECTION RESULT NEAR SURFACE
PARALLEL DETECT (WATER DISTANCE 20mm)

TP3
50
(FORM HOLES OF
φ0.5mm AT DEPTHS
3,5,7 AND 9mm)

ULTRASONIC DETECTION RESULT WITHIN BEARING
INNER DETECT OF φ0.5mm (WATER DISTANCE 15mm)

RADIAL LOAD BY HYDRAULIC PRESSURE

AXIAL LOAD BY HYDRAULIC PRESSURE

ULTRASONIC DETECTING METHOD FOR BEARING RING

BACKGROUND OF INVENTION

1. Field of Invention

The present invention relates to an ultrasonic detecting method suitable for a bearing ring of a tapered roller type rolling bearing or a cylindrical roller type rolling bearing such as a roll neck bearing for steel, in particular, to which a large load is applied.

2. Related Art

Conventionally, as an ultrasonic detecting method for detecting a defect within a bearing ring such as an inner race or an outer race, there has been known a normal bean method in which, during the manufacturing process of a steel product for a bearing ring, the steel product having been rolled is placed within the water or on a stand and an ultrasonic wave is transmitted from the outer peripheral surface to the inner portion of the steel product thereby to detect the defect of the bearing ring (see Special Steel, vol. 46, No. 6, page 31, edited by Special Steel Club Co.).

Further, as an ultrasonic detecting method for detecting a defect within or on the surface of a rolling element such as a ball, roller or the like, there has been employed in many cases a method in which an ultrasonic wave with a frequency in a rage of 15 MHz to 50 MHz is transmitted to the rolling element to detect a microscopic defect.

However, the aforesaid conventional ultrasonic detecting method for a steel product for a bearing ring mainly has been developed so as to detect a blow hole within the steel product or a defect such as a non-pressed portion or the like of the steel product in the rolling process, but not developed so as to detect a microscopic defect in the vicinity of the surface of the steel product or a large non-metallic intervening material of about several 100 $\mu$m within the steel product.

This is because the dead zone just beneath the surface of the steel product at the time of performing the ultrasonic detection is large since the surface of the steel product having been subjected to the rolling process and left as it is is rough. Further, since there is a bend, torsion or the like in the steel product, it is difficult to maintain the distance between the steel product and the probe constant, and in particular it is impossible to detect a microscopic defect in the vicinity of the surface of the steel product Furthermore, in the case of detecting a defect within the steel product with such a large diameter exceeding 100 mm, since it is required to set the detecting frequency to a low frequency in order to prevent the degradation of the sensitivity due to the attenuation of the ultrasonic wave, only a defect of about several mm can be detected.

The ultrasonic detecting method used for inspecting a rolling element mainly has been developed so as to efficiently detect a flaw or a microscopic surface defect of the rolling element. Such an object of this ultrasonic detecting method will be understood from a fact that a very high frequency in a rage of 15 MHz to 50 MHz capable of detecting a microscopic defect has been used in this method.

According to the recent technical development, it has become possible to detect a microscopic non-metallic intervening material of about 0.01 mm (10 $\mu$m), for example, by using the ultrasonic wave of a high frequency (e.g., 50 MHz to 150 MHz). However, if the frequency is made higher, the attenuation degree of the ultrasonic wave within the steel product becomes larger (the attenuation degree of the ultrasonic wave becomes further larger if the degree of the roughness of the surface of the steel product becomes larger), so that the defect detection can be performed only in the range from the surface of the steel product to a position beneath by about 3 mm from the surface, for example,. Accordingly, it has been impossible to efficiently inspect a product such as a bearing ring, in particular, which is required to be inspected as to a defect at the inner portion thereof.

The total amount of non-metallic intervening material contained in the steel product used for a bearing ring has been reduced due to the recent improvement of the steel manufacturing technique. In particular, the generation frequency of a defect such as a macro-streak-flaw or the like which is a typical example of a large non-metallic intervening material has been reduced. However, such a defect as a macro-streak-flaw or the like sometimes remains within a steel product, and hence there has been a case that the premature breakaway of the bearing occurs due to the macro-streak-flaw or the like. Accordingly, it has been desired to provide a method for effectively detecting in advance a defect such as a macro-streak-flaw or the like remained within a steel product in order to improve the reliability of a bearing.

For example, since a bearing such as a steel rolling bearing or the like is applied with a very large load, the maximum shearing stress appears within a steel product in a range from the position near the surface thereof to such a deep position of several mm from the surface thereof. Accordingly, it is required to detect not only a defect just beneath the surface of the steel product but also a defect at the deep position within the steel product.

An example of a method for detecting the distribution of relatively small non-metallic intervening material within a steel material by increasing the ultrasonic wave frequency is disclosed in Unexamined Japanese Patent Unexamined Publication Hei. 9-257761. However, in this method, since the detection is performed after adjusting the surface roughness of a sample of the steel product by the grinding finishing process, it is difficult to detect all the steel products.

SUMMARY OF THE INVENTION

The present invention has been intended to overcome the aforesaid conventional problems, and an object of the present invention is to provide an ultrasonic detecting method for a bearing ring which can accurately detect defects in the entire section from the surface to the inner portion of a bearing ring, in particular, a large non-metallic intervening material within the bearing ring thereby to provide the bearing ensured as to the non-presence of any defect therein.

In order to achieve the aforesaid object, an ultrasonic detecting method for a bearing ring according to the present invention is characterized in that, in the ultrasonic detecting method for the bearing ring in which a bearing ring and an ultrasonic detection probe are disposed within ultrasonic transmission medium such as water, then ultrasonic wave is transmitted from the ultrasonic detection probe to the bearing ring, and a defect of the bearing ring is detected on the basis of an ultrasonic wave echo reflected from the bearing ring, wherein at least a defect in a range from the surface of the bearing ring to a position beneath by 2 mm from the surface of the bearing ring which is deeper than a maximum shearing stress position of the bearing ring is detected by an angle beam method with an incident angle on a range of 10 to 30°, preferably in a range of 25 to 30°, and a defect in a range deeper than the range detected by the angle beam method is detected by a normal beam method with an incident angle in a range of 0 to 10°, preferably in a range of 0 to 5°, thereby to detect a defect in the entire section of the bearing ring.

In this case, it is preferable to use a focusing type probe having a strong directivity as the ultrasonic detection probe.

In the case of performing the ultrasonic detection as to the orbit plane of a rolling bearing, in particular, a tapered roller type bearing, since the raceway surface is complicated in the three-dimensional configuration along the axial direction of the bearing, it is difficult to make a probe closely contact to the orbit plane of the ring like a contact type manual detection method and so it is difficult to keep the incident condition of the ultrasonic wave constant.

Further, the tapered roller type bearing is not a rectangular shape when its detection orbit plane is developed. Thus, when a surface wave is used as the ultrasonic wave, the transmitted ultrasonic wave is reflected by the end face of the bearing in a short propagation distance, so that the defect detection range becomes narrow. As a consequence, there arises a unique problem that, it is required to move the probe several times during the detection procedure, so that the detection time becomes long.

In order to solve such a problem, the aforesaid soaking type normal beam method or angle beam method is employed under the detection condition set in accordance with a desired detection range thereby to make it possible to effectively detect a defect within the bearing ring.

As a result, the bearing ring detected by the ultrasonic detecting method of the present invention can be inspected that there is no defect in a range from the surface to the position deeper than the maximum shearing stress position of the bearing ring irrespective of the size of the bearing ring and so the non-presence of the inner defect of the bearing can be ensured.

An ultrasonic detecting method for a bearing ring of the present invention is provided in that, in the ultrasonic detecting method for the bearing ring in which a bearing ring and an ultrasonic detection probe are disposed within ultrasonic transmission medium such as water, then ultrasonic wave is transmitted from the ultrasonic detection probe to the bearing ring, and a defect of the bearing ring is detected on the basis of an ultrasonic wave echo reflected from the bearing ring, wherein the ultrasonic wave transmitted from the ultrasonic detection probe to the bearing ring is set to have a frequency not higher than 30 MHz, preferably in a range of 2 to 30 MHz, and, as the bearing ring to which the ultrasonic wave is transmitted, a bearing ring which is subjected to a thermosetting processing of hardening and tempering processings or a thermosetting processing of a carbonizing or carbonitriding processing and hardening and tempering processings and then subjected to a grinding processing is employed.

In this case, it is preferable to set the crystal grain size of the bearing ring after the thermosetting processing to No. 8 (old austenite grain size) or more in order to stabilize the structure thereof. Both the angle beam method and the normal beam method may be used as the ultrasonic detecting method.

Several kinds of heat histories are applied to the bearing during the manufacturing process thereof, and hence various kinds of metal structures are generated in the bearing ring.

It is known that the degree of the attenuation of the ultrasonic wave changes depending on the kind of the metal structure (see "Ultrasonic Detection Test A": Edition by Japanese Society for Nondestructive Testing (Co.), p.158). Accordingly, at the time of the detection of the bearing ring, it is necessary to use the most suitable metal structure.

Although the bearing ring is subjected to several heat histories during the manufacturing process thereof, in the hot forgoing method in which a bearing steel is heated to a high temperature of 1200° C. and then subjected to the forgoing process to form a bearing ring, the bearing ring having been subjected to the forgoing process is cooled by a self-cooling process or a fan-cooling process. In this case, the metal structure of the bearing ring may be varied in its structure configuration in such a manner that a part of the bearing ring is formed by the pearlite structure and the remaining part is formed by the martensite structure.

In the case of subjecting the bearing ring to the carbonizing or carbonitriding processing, the bearing ring is subjected to the heat histories such as the self-cooling process or the fan-cooling process in the cooling process after the carbonizing process, like the aforesaid manner. In this case, the metal structure of the bearing ring is unique as compared with that of the bearing steel and the carbonized steel has the carbon density gradient from its surface toward the inner portion thereof, so that the bearing ring has a partially unique structural configuration, in particular, a layered structure, as compared with the bearing steel.

The inventors of the present invention performed the detection as to the bearing ring having such different structural configurations and found that the attenuation of the ultrasonic wave becomes partially large due to the different structural configurations and found that it is difficult to detect the entire section of such a bearing ring having a thickness exceeding 10 mm.

Further, since the bearing ring contains large crystal grains or duplex grains of large and small crystal grains, a so-called tree-shaped echoes (a state where noises irregularly appear in a tree-shape near a defect signal and so the S/N of the defect signal is bad) appear in a manner that the ultrasonic wave is reflected by the crystal grains and the reflected wave is detected as echoes, so that it is difficult to distinguish the defect echoes from the tree-shaped echoes.

The inventors or the like of the present invention have found as the result of the search and research that the configuration of the metal structure most suitable for the detection of the bearing ring is the martensite structure which is formed by subjecting a bearing ring to the thermosetting processing of the hardening and tempering processings or the thermosetting processing of the carbonizing or carbonitriding processing and the hardening and tempering processings. The inventors found that, in this case, the degree of attenuation of the ultrasonic wave is small and the defect echoes is less influenced by the tree-shaped echoes.

When the frequency of the ultrasonic wave exceeds 30 MHz and reaches 50 MHz, even if the bearing ring whose structure has been adjusted is employed, the degree of attenuation of the ultrasonic wave becomes large and so it becomes difficult to detect the entire section of the bearing ring.

Some of the bearings are applied with a large load and so the bearing rings thereof are applied with shearing stress due to the rolling to the deep inner portions thereof. Accordingly, there has been needs to detect that the bearing ring does not contain any large intervening material in a range from the surface to the deep inner portion thereof as well as the portion near the surface thereof.

In view of the aforesaid matters, in the present invention, the ultrasonic detection for the bearing ring is performed by using the frequency not higher than 30 MHz.

Further, when the frequency is not higher than 2 MHz, although the degree of the attenuation of the ultrasonic wave is small, it is quite difficult to detect a small defect. Thus, the frequency is preferably not lower than 2 MHz.

DETAILED DESCRIPTION OF PREFERRED EMBODIMENTS

Embodiments of the present invention will be described with reference to the accompanying drawings.

Figure 1:
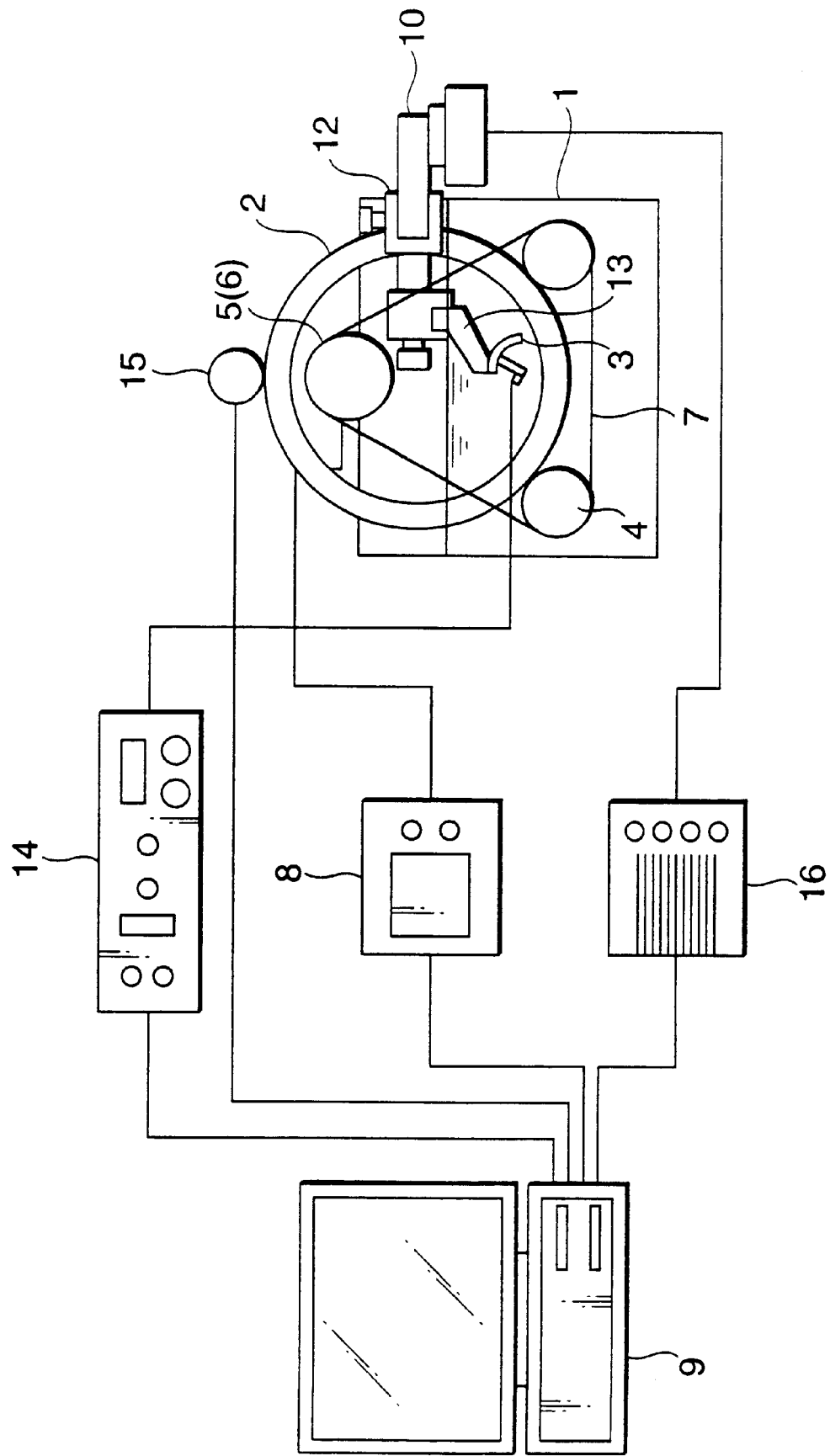
FIG. 1 is a schematic diagram showing an apparatus used for an ultrasonic detecting method for a bearing ring according to a first embodiment of the present invention.
Figure 2:
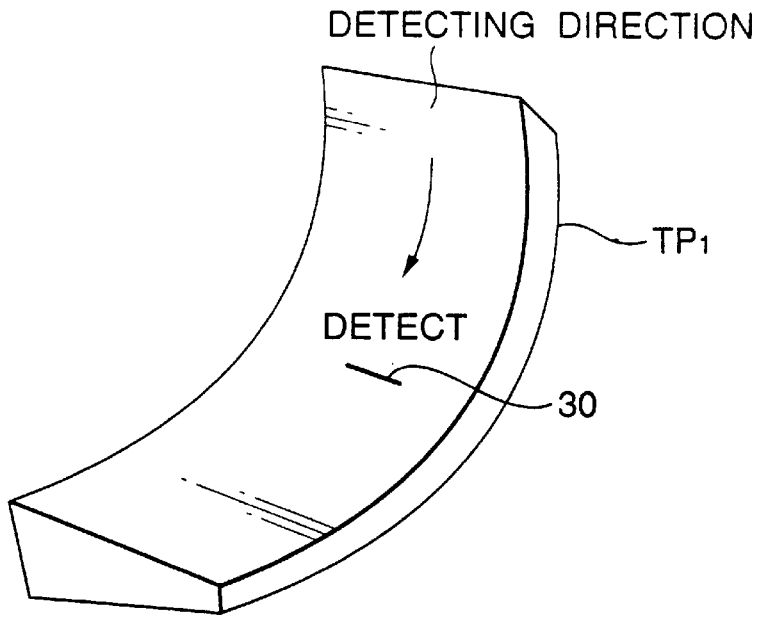
FIG. 2 is a perspective view showing a test piece provided with an artificial defect perpendicularly to a detecting direction (circumferential direction).
Figure 3:
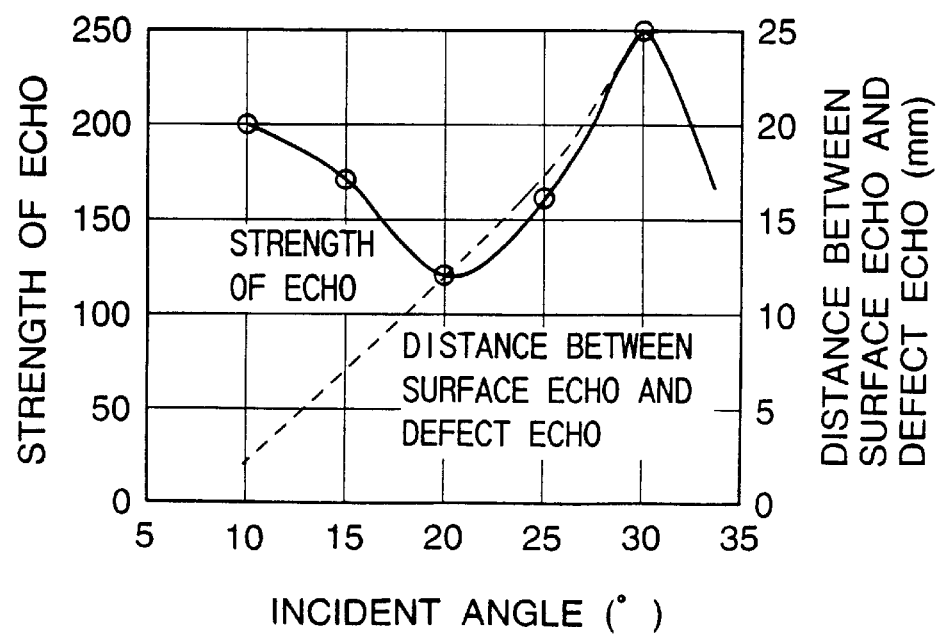
FIG. 3 is a graph showing the detected result in a case of performing the ultrasonic detection as to the test piece shown in FIG. 2.
Figure 4:
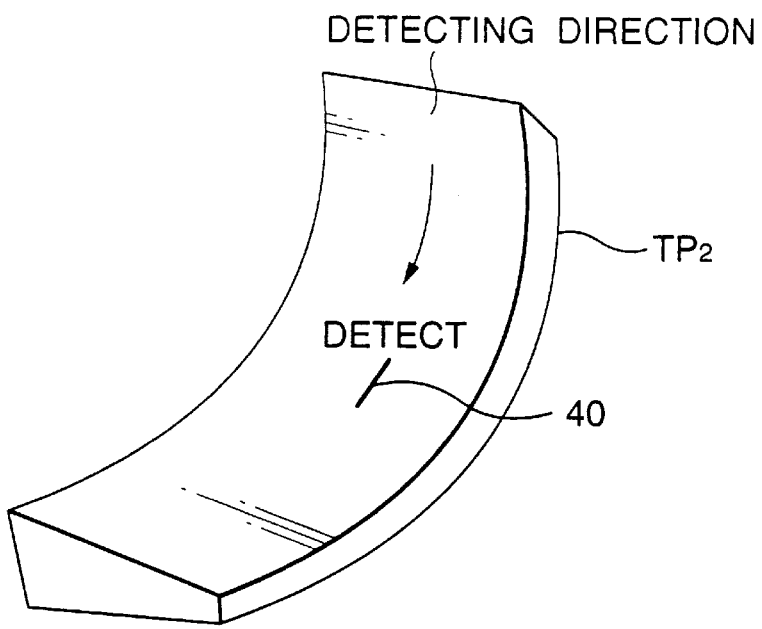
FIG. 4 is a perspective view showing a test piece provided with an artificial defect in parallel to a detecting direction (circumferential direction).
Figure 5:
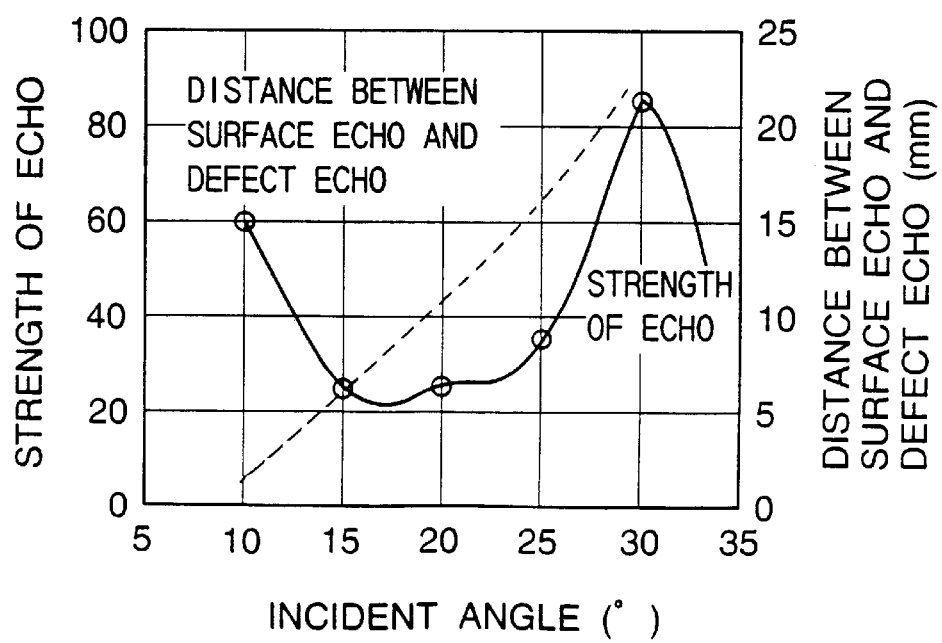
FIG. 5 is a graph showing the detected result in a case of performing the ultrasonic detection as to the test piece shown in FIG. 4.
Figure 6:
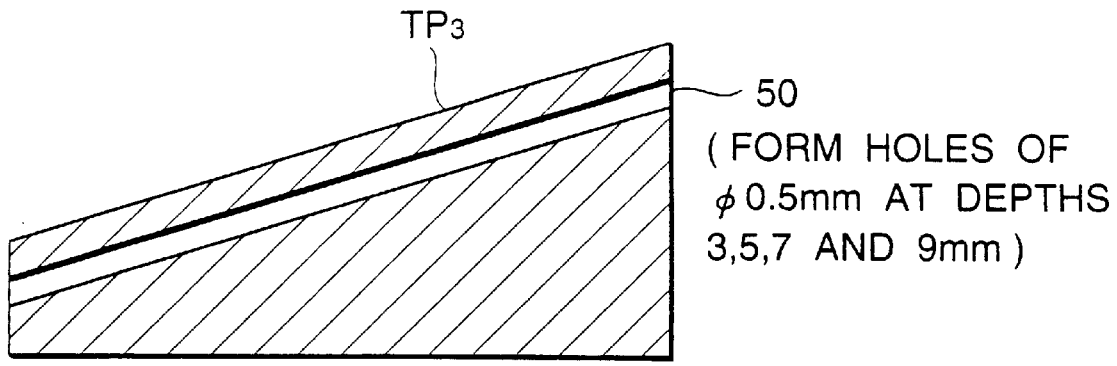
FIG. 6 is a sectional view showing a test piece provided with a hole of φ 0.5 mm perpendicularly to a detecting direction (circumferential direction) at a predetermined depth from the surface of the piece.
Figure 7:
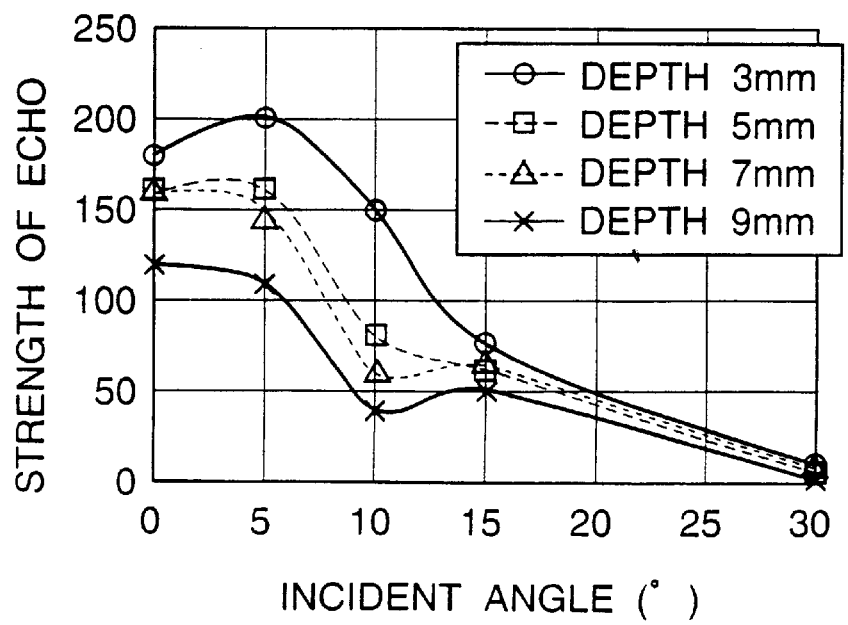
FIG. 7 is a graph showing the detected result in a case of performing the ultrasonic detection as to the test piece shown in FIG. 6.
Figure 8:
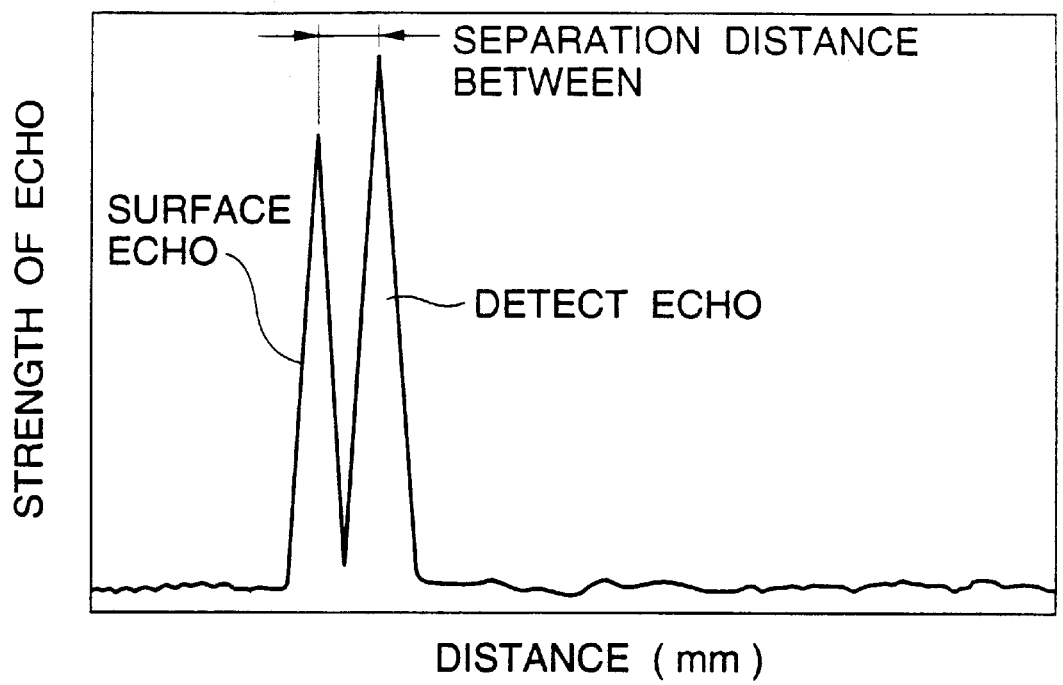
FIG. 8 is a graph showing the relation between a strength of reflection echo and a separation distance between surface echo and defect echo at the time of performing the detection with an incident angle of 10°.
Figure 9:
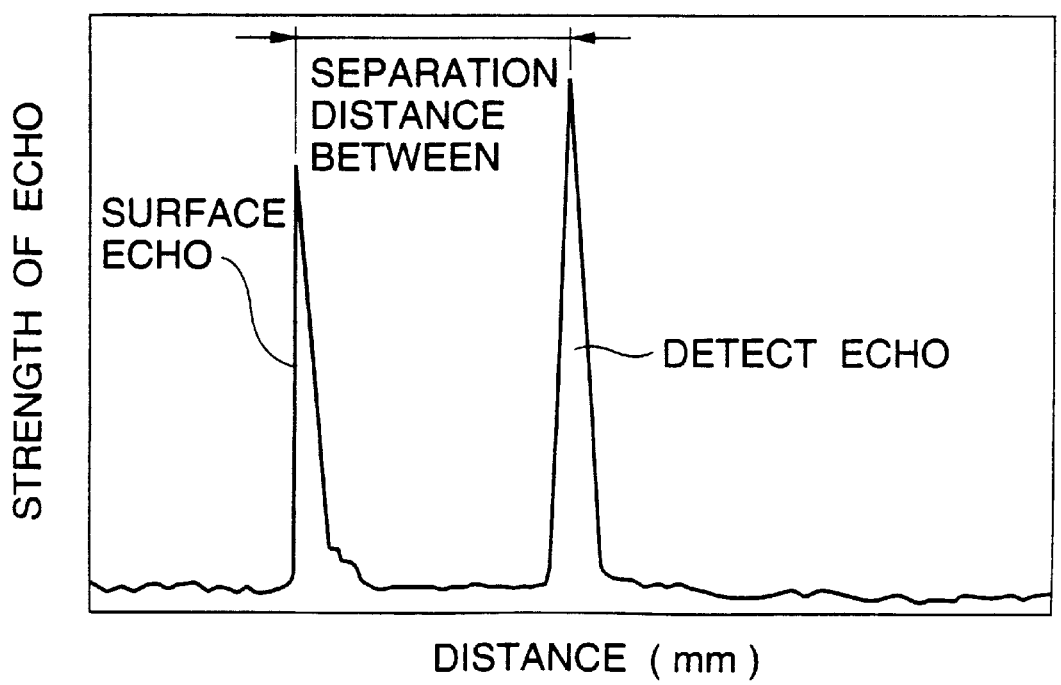
FIG. 9 is a graph showing the relation between a strength of reflection echo and a separation distance between surface echo and defect echo at the time of performing the detection with an incident angle of 30°.
Figure 10:
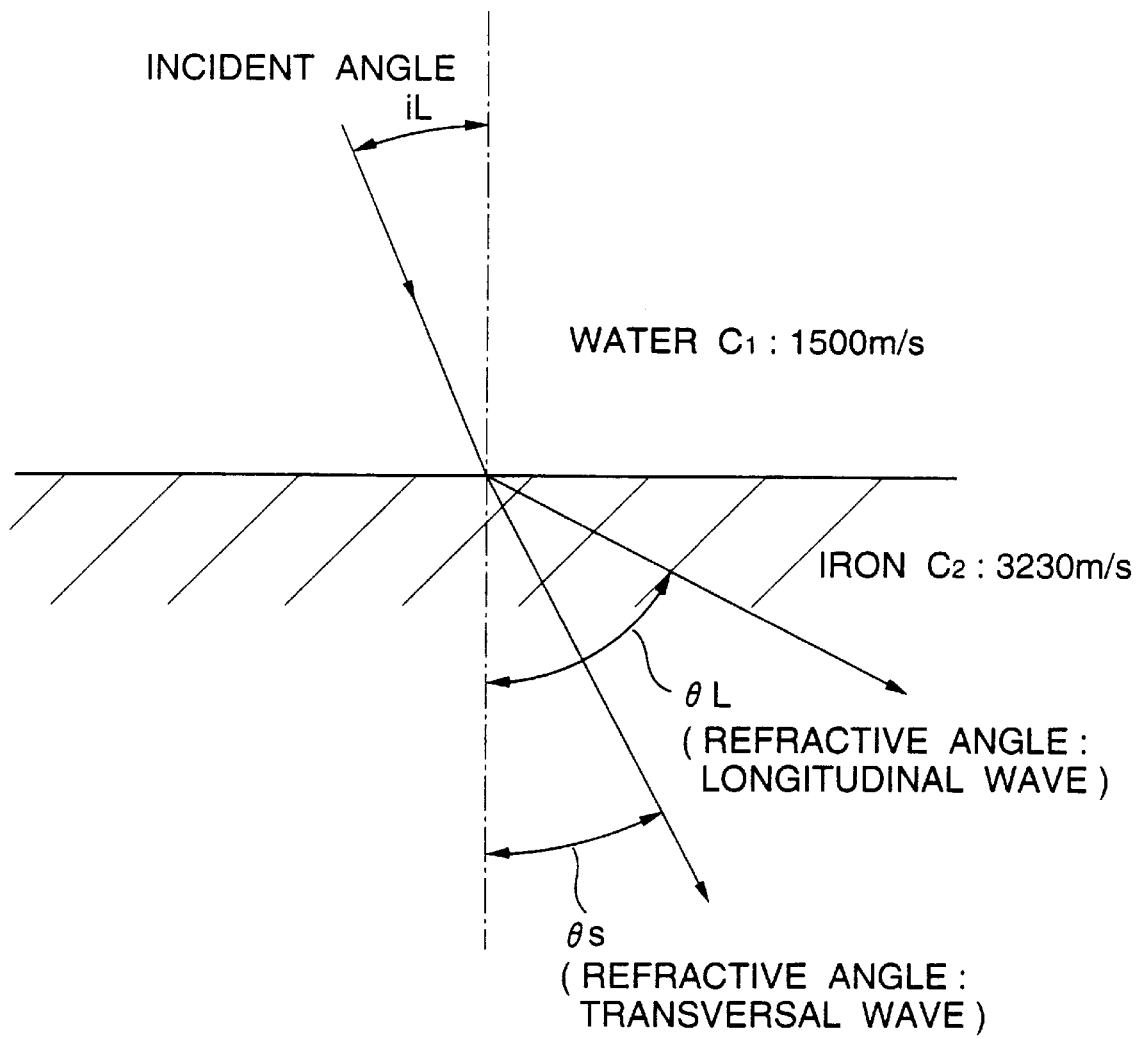
FIG. 10 is a diagram for explaining the relation between an incident angle and a refractive angle when an incident angle exceeds 30°.

FIG. 1 is a schematic diagram showing an apparatus used for an ultrasonic detecting method for a bearing ring according to a first embodiment of the present invention. FIG. 2 is a perspective view showing a test piece provided with an artificial defect perpendicularly to a detecting direction (circumferential direction). FIG. 3 is a graph showing the detected result in a case of performing the ultrasonic detection as to the test piece shown in FIG. 2. FIG. 4 is a perspective view showing a test piece provided with an artificial defect in parallel to a detecting direction (circumferential direction). FIG. 5 is a graph showing the detected result in a case of performing the ultrasonic detection as to the test piece shown in FIG. 4. FIG. 6 is a sectional view showing a test piece provided with a hole of φ 0.5 mm perpendicularly to a detecting direction (circumferential direction) at a predetermined depth from the surface of the piece. FIG. 7 is a graph showing the detected result in a case of performing the ultrasonic detection as to the test piece shown in FIG. 6. FIG. 8 is a graph showing the relation between a strength of reflection echo and a separation distance between surface echo and defect echo at the time of performing the detection with an incident angle of 10°. FIG. 9 is a graph showing the relation between a strength of reflection echo and a separation distance between surface echo and defect echo at the time of performing the detection with an incident angle of 30°. FIG. 10 is a diagram for explaining the relation between an incident angle and a refractive angle when an incident angle exceeds 30°.

An ultrasonic detecting apparatus will be explained.

In FIG. 1, a reference numeral 1 depicts a water tank in which water serving as ultrasonic wave transmission medium is stored. The outer ring of a tapered roller type rolling bearing as a bearing ring 2 and an ultrasonic detection probe 3 are disposed within the water tank 1 in a dipped state. A focusing type probe having a strong directivity and hardly influenced by the curvature of the bearing ring 2 is employed as the ultrasonic detection probe 3.

The bearing ring 2 is placed on two pulleys 4 which are separately disposed along the horizontal direction. A belt 7 is wound in an equilateral triangular shape around the respective pulleys 4 and a pulley 6 which is fixed to the motor shaft of a rotation driving motor 5.

The rotation driving motor 5 is controlled by a control device 9 through a motor drive control amplifier 8 so that the bearing ring 2 placed on the pulleys 4 is rotated at a predetermined speed in accordance with the rotation of the rotation driving motor 5. The control device 9 is formed by a personal computer or the like having a display means such as a cathode ray tube (CRT) or the like.

The ultrasonic detection probe 3 is attached through a probe attachment 13 to an XY stage 12 of a linear guide device 10 disposed to be movable along the axial direction of the bearing ring 2 in a manner that the ultrasonic detection probe is disposed in the attached state so as to oppose to the inner periphery of the bearing ring 2. The ultrasonic detection probe 3 transmits ultrasonic pulses toward the inner periphery of the bearing ring 2 in accordance with a voltage signal supplied from an ultrasonic detecting device 14, then receives echo reflected from the inner periphery of the bearing ring, then converts the received echo into a voltage signal and transmits the voltage signal thus converted to the ultrasonic detecting device 14.

The ultrasonic detecting device 14 transmits a command signal formed by the voltage signal in accordance with a command from the control device 9 to the ultrasonic detection probe 3, then obtains defect detection information on the basis of the transmitted command signal and the received voltage signal and transmits the defect detection information to the control device 9. The control device 9 displays the defect detection information on the CRT.

The linear guide device 10 is adapted to move the ultrasonic detection probe 3 to the axial direction of the bearing ring 2 by means of a not-shown serve motor controlled by a linear guide controller 16. When it is detected that the bearing ring 2 has rotated one revolution (360°) by a rotary encoder 15 provided at the outer peripheral surface of the bearing ring 2, the linear guide controller 16 controls the servo motor on the basis of the command from the control device 9 to move the ultrasonic detection probe 3 to the axial direction of the bearing ring 2 by a predetermine distance. According to such a configuration, the entire section of the bearing ring 2 can be detected.

The ultrasonic detecting method according to the first embodiment of the present invention will be explained with reference to FIGS. 1 to 10.

Referring to FIG. 1, the outer ring of the tapered roller type rolling bearing with an inner diameter of 350 mm is employed as the bearing ring 2, and the bearing ring 2 is dipped into the water within the water tank 1 together with the focusing type probe (frequency of 10 MHz and resonator diameter of 6 mm) as the ultrasonic detection probe 3. In this state, the entire section of the bearing ring 2 is detected, while rotating the bearing ring 2 and moving the ultrasonic detection probe 3 toward the axial direction of the bearing ring 2, as to a defect in a range from the raceway surface (inner peripheral surface) of the bearing ring 2 to a position beneath by 2 mm from the surface which is deeper than the maximum shearing stress position of the bearing ring 2 and also as to a defect in a range deeper than that range.

The water distance (a distance between the inner peripheral surface of the bearing ring 2 and the ultrasonic detection probe 3) is set to be 20 mm in the case of performing the angle beam detection in a range from the raceway surface of the bearing ring 2 to a position just beneath by 2 mm from the surface, while the water distance is set to be 15 mm in the case of performing the normal beam detection in a range deeper than that range.

First, the explanation will be made as to the detection in the range from the raceway surface of the bearing ring 2 to a position just beneath by 2 mm from the surface. As shown in FIG. 2, a test piece TP1 is formed in a manner that an artificial defect 30 with a length of 10 mm, a width of 0.5 mm and a depth of 0.5 mm is provided so as to be perpendicular to the detecting direction (circumferential direction) on the orbit plane of the bearing ring 2. Then, the detection is performed by using the ultrasonic detecting device of FIG. 1 in a manner that the incident angle (an angle inclined toward the circumferential direction with respect to a normal line set on the orbit plane) of the ultrasonic wave transmitted from the ultrasonic detection probe 3 is changed in a range of 5 to 35°.

The result of this detection will be shown in FIG. 3.

As clear from FIG. 3, it found to be possible to detect the artificial defect 30 by the angle beam detection with the incident angle in a range of 10 to 30°, and the best sensitivity was obtained when the incident angle is set at 30° as the detection condition.

Also the high detection sensitivity was obtained when the incident angle is set at 10°. However, in this case, since the positions (distance of the maximum heights) of the surface echo and the defect echo (a signal outputted only when a defect exists) are close to each other, although it is possible for a person to visibly discriminate these echoes but difficult for the detection device to automatically discriminate these echoes. Accordingly, the incident angle in a range of 25 to 30° is suitably as the detection condition since the surface echo and the defect echo are sufficiently separated in this condition.

FIGS. 8 and 9 show the detection results displayed on the CRT of the personal computer when the detections were performed with the incident angles of 10° and 30°, respectively.

It will be understood from these results that the distance between the surface echo and the defect echo at the time of the incident angles of 10° is shorter than that at the time of the incident angles of 30°.

As shown in FIGS. 4, a test piece TP2 is formed in a manner that an artificial defect 40 with a length of 10 mm, a width of 0.5 mm and a depth of 0.5 mm is provided so as to be in parallel to the detecting direction (circumferential direction) on the orbit plane of the bearing ring 2. Then, the detection is performed by using the ultrasonic detecting device of FIG. 1 in a manner that the incident angle (an angle inclined toward the circumferential direction with respect to a normal line set on the orbit plane) of the ultrasonic wave transmitted from the ultrasonic detection probe 3 is changed in a range of 5 to 35°.

The result of this detection will be shown in FIG. 5.

As clear from FIG. 5, it found to be possible to detect the artificial defect 40 by the angle beam detection with the incident angle in a range of 10 to 30°, and the best sensitivity was obtained when the incident angle is set at 30° as the detection condition, like the aforesaid example.

Also the high detection sensitivity was obtained when the incident angle is set at 10°. However, in this case, since the positions (distance of the maximum heights) of the surface echo and the defect echo are close to each other, the incident angle in a range of 25 to 30° is suitably as the detection condition since the surface echo and the defect echo are sufficiently separated in this condition, by the same reason as the aforesaid example.

Then, the explanation will be made as to the case where the angle beam method was performed at the incident angle exceeding 30°.

With reference to FIG. 10, when the ultrasonic wave is made incident within a subject to be detected such as iron, steel or the like with an incident angle of $i_L$, the ultrasonic wave is divided into a transversal wave and a longitudinal wave, and then the longitudinal wave and the transversal wave propagate with refractive angles of θL and θs, respectively, where θL>θs. When the ultrasonic wave is transmitted within the water and the steel, the relation between the incident angle and the refractive angle as to the transversal wave will be represented as follows.

$$\sin \theta_s = C_2/C_1 \times \sin i_L \qquad (1)$$

$$\sin \theta_s = 3230/1500 \times \sin (i_L) \qquad (2)$$

$$\theta_s < 90°$$

where $C_1$ represents the sound velocity of 1500 m/s within the water, and $C_2$ represents the sound velocity of 3230 m/s within the iron.

The ultrasonic detection probe 3 serves as a receiver as well as a resonator, and, at the time of receiving a signal (defect signal), receives the signal returning through a reverse path (same as the path for the transmission signal). The strength of the echo shown in the ordinate in each of FIGS. 3, 5, 8, 9 represents the strength of the echo returned to the water side from the iron or steel side, and the signal thus returned may be either one of or both the transversal and longitudinal waves.

when the incident angle $i_L$ becomes not smaller than a predetermined value, the refractive angle within the iron or steel becomes not smaller than 90°. In this case, the defect signal merely propagates on the surface of the iron or steel or reflected therefrom and hence is not returned to the ultrasonic detection probe 3.

As described above, supposing that the refractive angle θL of the longitudinal wave is larger than the refractive angle θs of the transversal wave with respective to the incident angle $i_L$ and that either one of the longitudinal and transversal waves respectively propagated with the refractive angles of θL and θs may be returned, it will be enough to consider the limit of the incident angle capable of returning the transversal wave propagated with the refractive angle θs.

The limit of the incident angle in this case will be about 28° from the aforesaid expressions (1) and (2) supposing that the refractive angle θs is theoretically 90°. However, since the ultrasonic wave is outputted with a certain velocity range, the defect can be detected sufficiently with the incident angle of 30° or less. Accordingly, as shown in FIGS. 3 and 5, the defect signal reduces abruptly when the incident angle exceeds 30°. Thus, the limit of the incident angle at the time of performing the angle beam detection is 30°.

Then, the explanation will be made as to the detection in the range deeper than the position just beneath by 2 mm from the surface.

As shown in FIG. 6, a test piece TP3 is formed in a manner that holes (artificial defects) 50 with a diameter of φ 0.5 mm are individually provided at depths of 3, 5, 7 and 9 mm so as to be perpendicular to the detecting direction (circumferential direction) on the orbit plane of the bearing ring 2. Then, the detection is performed by using the ultrasonic detecting device of FIG. 1 in a manner that the incident angle (an angle inclined toward the circumferential direction with respect to a normal line set on the orbit plane) of the ultrasonic wave transmitted from the ultrasonic detection probe 3 is changed in a range of 0 to 30°.

The result of this detection will be shown in FIG. 7.

As clear from FIG. 7, it found to be preferable to detect defects at the respective depths by the normal beam detection with the incident angle in a range of 0 to 10°, and the best sensitivity as to the defect detection was obtained at the respective depths when the incident angle was set in a range of 0 to 5° as the detection condition.

Accordingly, it will be understood that the incident angle in a range of 0 to 5° is more preferable. When the incident angle is 0°, the vertical wave is transmitted to the defect along the path of the shortest distance, so that the distance between the surface echo and the defect echo becomes short. Thus the slightly inclined incident angle of 5° is most preferable in view of sufficiently separating the surface echo and the defect echo.

As clear from the aforesaid description, according to the embodiment, it becomes possible to perform the ultrasonic detection on the orbit plane of the bearing ring which has been difficult due to the complicated configuration of the orbit plane of the bearing ring.

Thus, since the defects in the entire section from the surface of the bearing ring to the inner portion thereof can be detected with a high accuracy and in a short time, the early or short-life breakage due to the inner defect can be prevented effectively and so the non-presence of the inner defect of the bearing can be ensured.

EXAMPLE

The detection has been performed as to 300 bearing rings 2 under the condition that an outer ring of a tapered roller type rolling bearing with an inner diameter of 350 mm serving as the bearing ring 2 is set in the ultrasonic detecting apparatus shown in FIG. 1, then the bearing ring 2 is driven at the rotation speed of 800 mm/s, and the detection pitch toward She axial direction of the bearing ring is set at 0.6 mm.

In this case, the detection in a range from the raceway surface of the bearing ring 2 to a position just beneath by 2 mm from the surface thereof was performed by the angle beam method with an incident angle of 30°, while the detection in a range deeper than 2 mm from the raceway surface was performed by the normal beam method with an incident angle of 5°.

As a result of the detection of 300 bearing rings 2, the echoes which seem to be caused by the defects were found in three bearing rings in a manner that the echo was observed at the vicinity of the surface as to one of the three bearing rings and the echoes were observed at the inner portions as to the remaining two thereof. These three bearing rings were cut and ground, and the defect portions thereof were examined in detail, whereby the defect with a width of about 0.1 to 0.2 mm and a length of 0.2 to 0.4 mm at the maximum was found in each of these bearing rings and, as a result of the analysis, it was found that these defects are large non-metallic intervening material.

The ultrasonic detecting method for a bearing ring according to the second embodiment of the present invention will be explained with reference to FIGS. 11 to 13.

Figure 11:
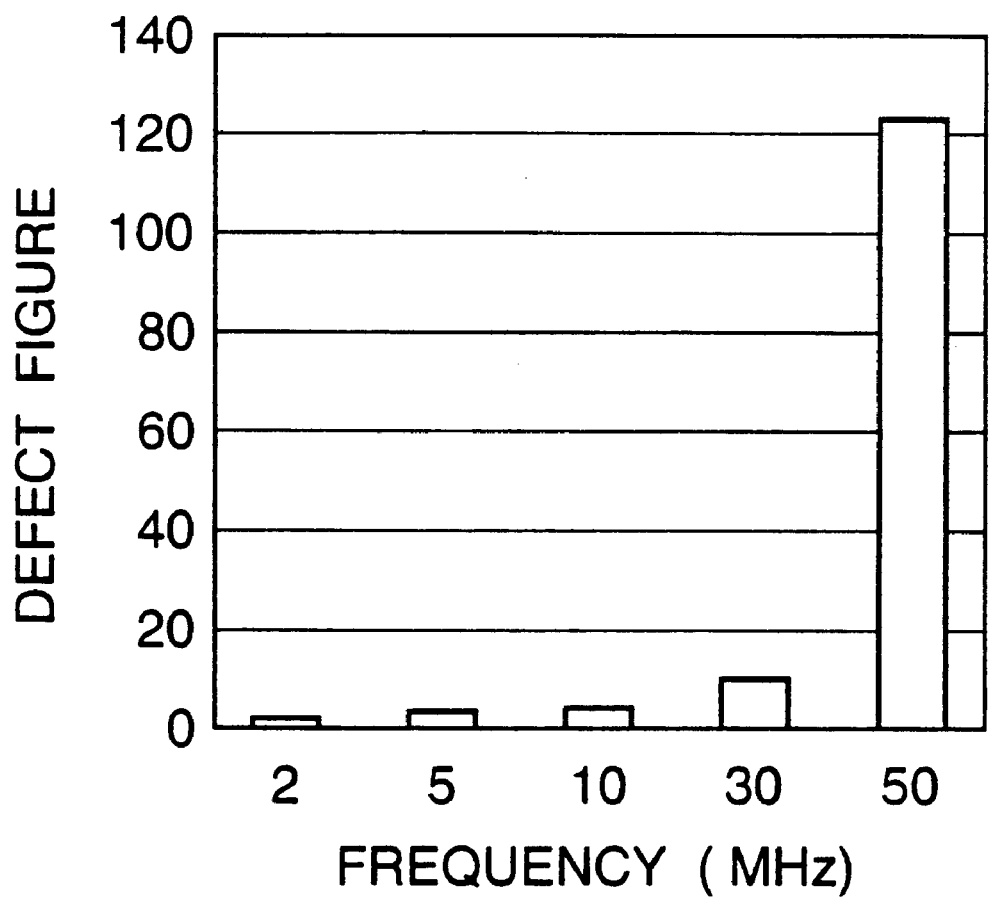
FIG. 11 is a graph showing the relation between defect figures and ultrasonic wave frequencies in the case where the ultrasonic detecting method for a bearing ring according to the second embodiment of the present invention is executed.
Figure 12:
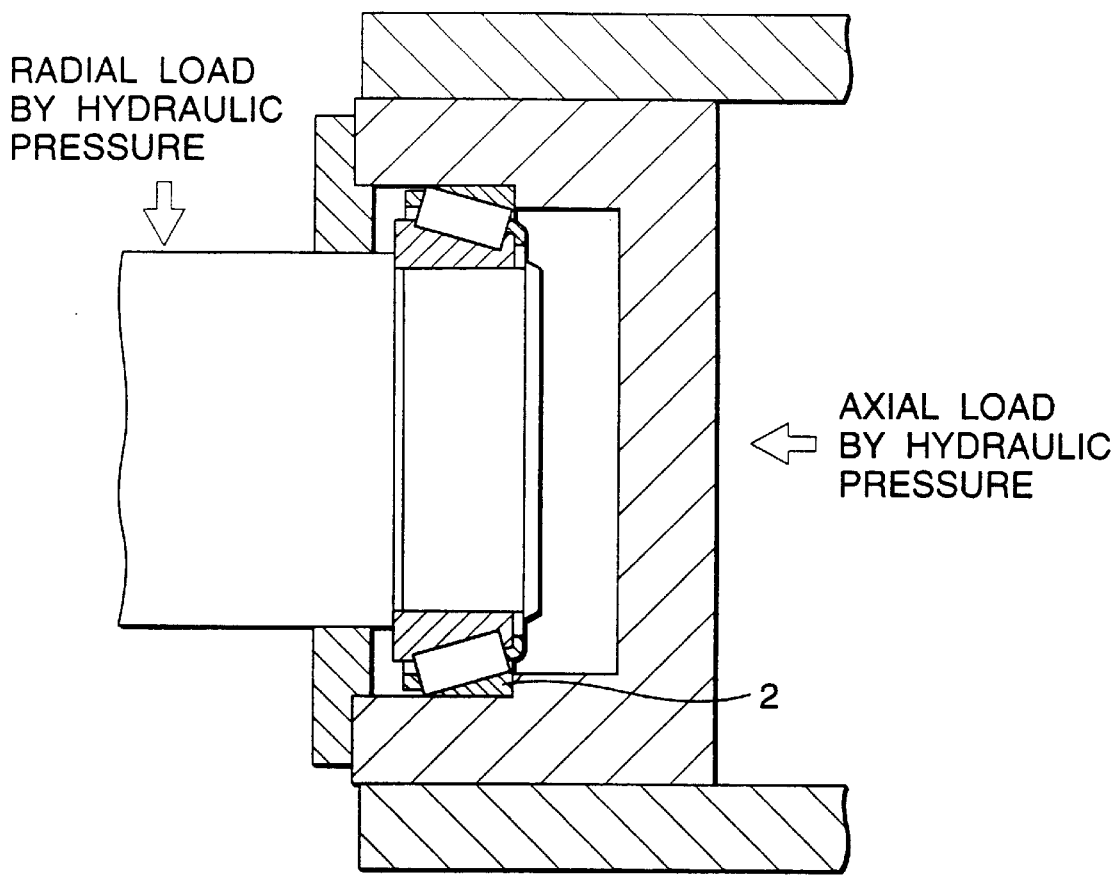
FIG. 12 is a schematic sectional view snowing a life time test device.

FIG. 11 is a graph showing the relation between defect figures and ultrasonic wave frequencies in the case where the ultrasonic detecting method for a bearing ring according to the second embodiment of the present invention is executed. FIG. 12 is a schematic sectional view showing a life time test device. FIG. 13 is a graph showing the relation between life time reducing rates and ultrasonic wave frequencies.

According to the embodiment, an outer ring of the tapered roller type rolling bearing is subjected to the thermosetting processing of the hardening and tempering processings (or the thermosetting processing of the carbonizing or carbonitriding processing and the hardening and tempering processings) in order to reduce the attenuation of the ultrasonic wave and so as to be less influenced by the tree-shaped echoes thereby to form martensite structure having the crystal grain size of No. 8 or more after the thermal processing. Then the outer ring is subjected to the grinding processing to finally form an outer ring of the tapered roller type rolling bearing HR32017 as the bearing ring 2. The detection of the entire section as to each of 300 bearing rings 2 thus formed was performed by using the ultrasonic detecting apparatus of FIG. 1 in a manner that each of the bearing rings is detected sequentially at respective frequencies of 2, 5, 10, 30 and 50 MHz in the order of lower frequency by using the ultrasonic detection probes 3 of the respective frequencies.

In this detecting procedure, the bearing ring 2 in which the defect was detected at one of the respective frequencies is eliminated from the subject for the succeeding detecting operation, and so only the bearing rings 2 in which no defect have been detected are used for the succeeding detecting operation using the higher frequency.

Although both the angle beam method and the normal beam method can be used as the ultrasonic detecting method, the angle beam method was employed in this embodiment.

The defect figures shown in the ordinate in FIG. 11 represent the average numbers of the defects of the bearing ring 2 found at the respective frequencies 5, 10, 30 and 50 MHz under the condition that the number of the defect within the bearing ring 2 found at the time of performing the detection at the frequency of 2 MHz is supposed to be 1.

As clear from FIG. 11, it will be understood that the number of the defects per one bearing ring among the bearing rings 2 in which the defects have been detected increases abruptly when the frequency exceeds 30 MHz.

According to the frequency characteristics of the ultrasonic wave, only relatively large defects can be detected by the low frequencies. When the frequencies are set to high values, small defects as well as large defects can be detected, so that it will be well understood that in the bearing ring 2 there are many defects such as small intervening material or the like detected by the frequency exceeding 30 MHz.

Next, a bearing was prepared by using the bearing ring 2 in which defects were detected at the respective frequencies, and the life time test of such a bearing has been performed by using the life time test device under the following condition.

a bearing: a tapered roller type rolling bearing HE32017XJ a radial load: 35750N an axial load: 15680N the rotation speed of an inner ring: 1500 rpm lubricator: grease The life time test was performed as to the bearing rings 2 in which the defects were detected at the respective frequencies thereby to obtain life times $L_{10}$. Then, in the case where the life time $L_{10}$ of the bearing ring 2 in which a defect was detected under the condition of the frequency of 50 MHz is supposed to be 100, the life time reducing rate of the life time $L_{10}$ of the bearing ring 2 in which a defect was detected at the frequency not higher than 30 MHz with respect to the life time $L_{10}$ of the former bearing ring 2 was obtained as the life time evaluation. The result of the test is shown in FIG. 13.

Figure 13:
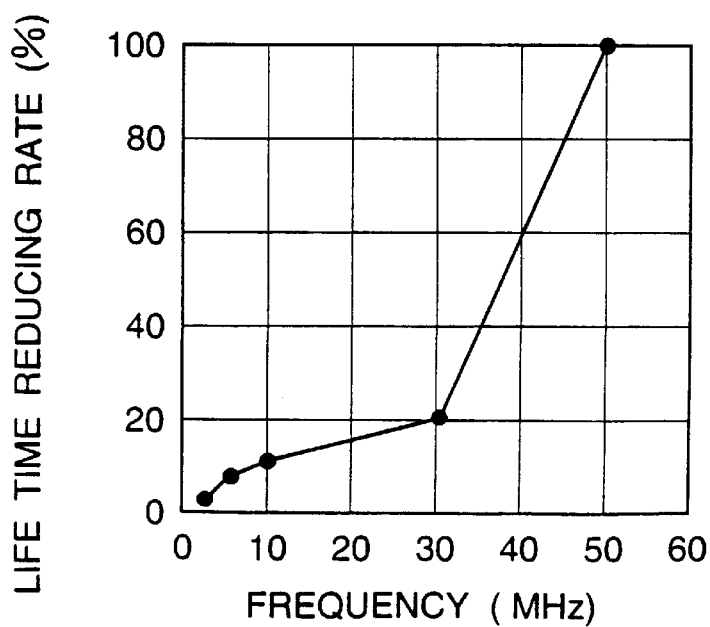
FIG. 13 is A graph showing the relation between life time reducing rates and ultrasonic wave frequencies.
Figure 14:
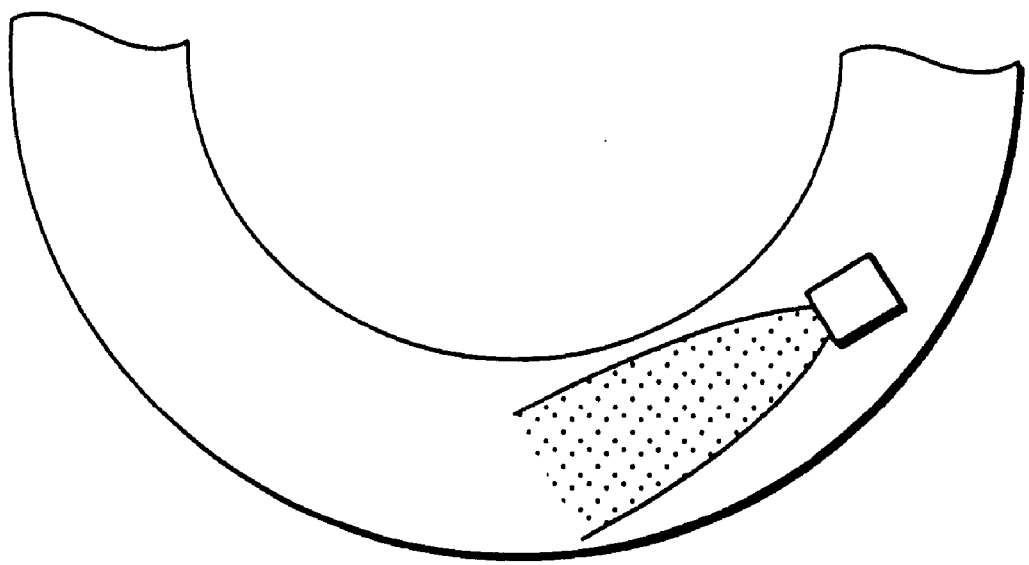
FIG. 14 is a diagram showing an outer ring of a tapered roller type rolling bearing developed in a plane and for explaining that it is difficult to detect a defect thereof merely by using a surface wave since the outer ring is not a rectangular shape like a cylindrical surface when developed in a plane.

As clear from FIG. 13, the life time of the bearing ring 2 in which a defect was detected at the frequency not higher than 30 MHz is quite shorter than that of the bearing ring 2 in which a defect was detected at the frequency of 50 MHz.

Although it is possible to detect a defect by using the frequencies not higher than 2 MHz, it is quite difficult to detect a small defect within the bearing ring 2 when using such frequencies. Thus, the frequency is preferably in a range of 2 MHz to 30 MHz.

As clear from the aforesaid description, according to the present embodiment, since the ultrasonic detection was performed as to the bearing ring of the martensite structure at the frequency not higher than 30 MHz, the defects in the entire section from the surface of the bearing ring to the inner portion thereof can be detected with a high accuracy and in a short time. Thus, a defect such as intervening material or the like largely influencing on the shortage of the life time of a bearing can be detected effectively. As a result, the early or short-life breakage due to the inner defect can be prevented effectively and so the non-presence of the inner defect of the bearing can be ensured.

As described above, according to the present invention, the defects in the entire section from the surface of the bearing ring to the inner portion thereof, in particular, the presence of a large non-metallic intervening material within the bearing ring can be detected with a high accuracy. As a consequence, the early or short-life breakage due to the inner defect can be prevented effectively and so the non-presence of the inner defect of the bearing can be ensured.

What is claimed is:

1. An ultrasonic detecting method for a bearing comprising the steps of:

disposing a desired surface of a bearing ring to be measured and an ultrasonic detection probe within ultrasonic transmission medium;

transmitting an ultrasonic wave from said ultrasonic detection probe to said measured surface of said bearing ring; and detecting a defect of said bearing ring on a basis of an ultrasonic wave echo reflected from said bearing ring, wherein at least a defect in a range from a surface of said bearing ring to a position beneath by 2 mm from a raceway surface of said bearing ring is detected by an angle beam method and a defect in a range deeper than said range detected by said angle beam method is detected by a normal beam method, thereby to detect a defect in an entire section of said bearing ring.

2. An ultrasonic detecting method as claimed in claim 1, wherein said angle beam method is performed under the condition that an incident angle with respect to said surface of said bearing ring is in a range of 10° to 30° and said normal beam method is performed under the condition that an incident angle with respect to said surface of said bearing ring is in a range of 0° to 10°.

3. An ultrasonic detecting method as claimed in claim 1, wherein said bearing ring contains the martensite structure subjected by hardening process.

4. An ultrasonic detecting method as claimed in claim 1, a crystal grain size of said bearing ring is not more than 25 $\mu$m in average of diameter thereof (JIS grain size No. 8).

5. An ultrasonic detecting method as claimed in claim 1, wherein said ultrasonic wave has a frequency in a range of 2 to 30 MHz.

6. An ultrasonic detecting method as claimed in claim 1, wherein said angle beam method is performed under the condition that an incident angle with respect to said surface of said bearing ring is in a range of 25° to 30° and said normal beam method is performed under the condition that an incident angle with respect to said surface of said bearing ring is in a range of 0° to 5°.

7. A ultrasonic defect detecting apparatus for detecting a defect of a bearing ring comprising:

an ultrasonic defect detecting probe for irradiating an ultrasonic wave to a measured surface of said bearing ring and for receiving an ultrasonic wave echo reflecting from said measured surface of said bearing ring;

an ultrasonic detecting wave transmission medium interposed between said measured surface and said probe;

rotation drive means for rotating said bearing ring in a circumferential direction;

probe scanning means for scanning said ultrasonic defect detecting probe in an axis direction of said bearing ring with respect to said measured surface;

bearing ring rotation position detecting means for detecting a rotation position of said bearing ring in circumference direction of said bearing ring; and a ultrasonic defect judgement device for judging whether or not a defect exist in said bearing ring on the basis of said ultrasonic echo signal of said ultrasonic defect detecting probe under the condition that a desired surface to be measured is selected by said probe scanning means and bearing ring rotation position detecting means.

* * * * *